United States Patent [19]

Labeeuw et al.

[11] Patent Number: 4,609,654

[45] Date of Patent: Sep. 2, 1986

[54] DERIVATIVES OF CEPHALOSPORINS SUBSTITUTED IN 3 POSITION BY A THIOMETHYL HETEROCYCLE GROUP; AND PHARMACEUTICAL COMPOSITIONS CONTAINING THEM

[75] Inventors: Bernard Labeeuw, Montpellier; Ali Salhi, Saint-Gely-du-Fesc, both of France

[73] Assignee: Sanofi, Paris, France

[21] Appl. No.: 443,933

[22] Filed: Nov. 23, 1982

[30] Foreign Application Priority Data

Dec. 1, 1981 [FR] France ................................ 81 22506

[51] Int. Cl.[4] .................. C07D 501/46; A61K 31/545

[52] U.S. Cl. .................................... 514/206; 540/225; 540/227

[58] Field of Search .................... 544/27, 25; 424/246; 514/206

[56] References Cited

U.S. PATENT DOCUMENTS 4,165,430 8/1979 Bradshaw et al. .................... 544/22

4,237,128 12/1980 Cimarusti et al. .................... 544/21

4,315,005 2/1982 Ayrs et al. .......................... 424/246

FOREIGN PATENT DOCUMENTS 866038 12/1952 Fed. Rep. of Germany .

1603212 11/1981 United Kingdom .

*Primary Examiner*—Nicholas S. Rizzo

*Attorney, Agent, or Firm*—Weingarten, Schurgin, Gagnebin & Hayes

[57] ABSTRACT

The present invention relates to new cephalosporins of general formula

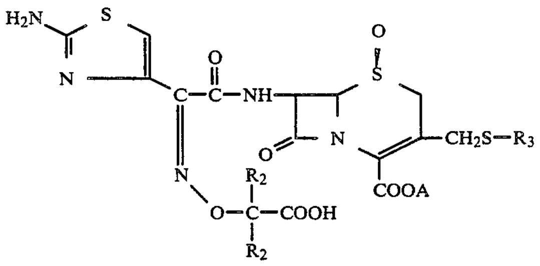

(II)

in which $R_1=R_2=CH_3$ or $R_1$ and $R_2$ together form a 1,3-propylene group, A is H, a cation, an ester or a hemiacetal, and $R_3$ is a heterocycle comprising five or six atoms including at least one atom in the ring of nitrogen. It also relates to a process for preparing these cephalosporins and to the drugs containing them.

6 Claims, No Drawings

DERIVATIVES OF CEPHALOSPORINS SUBSTITUTED IN 3 POSITION BY A THIOMETHYL HETEROCYCLE GROUP; AND PHARMACEUTICAL COMPOSITIONS CONTAINING THEM

The present invention relates to new derivatives of cephalosporins, to a process for preparing same and to pharmaceutical compositions containing said derivatives of cephalosporins as active ingredients.

More particularly, the invention relates to new cephalosporins substituted in 3 position by a $CH_2$—S—Het group, in which Het denotes a heterocycle with 5 ring atoms comprising at least 2 atoms of nitrogen and possibly one atom of sulfur or a heterocycle with 6 ring atoms comprising 1 atom of nitrogen.

Belgian Pat. No. 866 038 cites or describes inter alia a series of sulfoxides of cephalosporins corresponding to general formula:

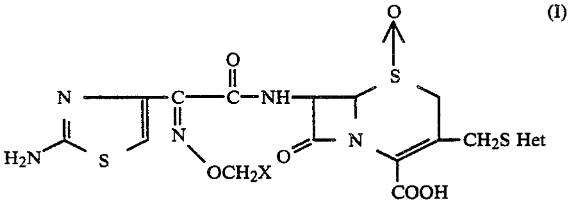
(I)

X = H, COOH in which Het represents a heterocycle with 5 or 6 ring atoms and in particular a 1,2,3-triazole, a 1,3,4-triazole, a 1,3,4-thiadiazole, a tetrazole or a 2-pyridyl group, possibly substituted.

The cephalosporins of formula (I) are generally supposed to possess a very considerable bacterial activity against Gram positive and Gram negative bacteria and to be effective against penicillinase-producing staphylococci.

The present invention relates to new cephalosporins which possess a bacterial profile very different from that of the compounds of the above-mentioned Patent. In fact, the compounds of the invention have remakable activity on enterobacteria, including those producing $\beta$-lactamases, while they are very weakly active on staphylococci.

These new cephalosporins correspond to general formula:

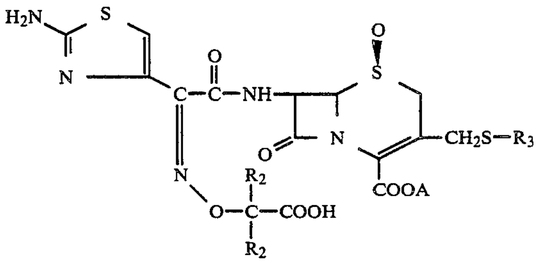
(II)

in which:

$R_1$ and $R_2$, taken separately, each represent a methyl group or $R_1$ and $R_2$ taken together represent a 1,3-propylene group, $R_3$ represents a heterocycle of formula:

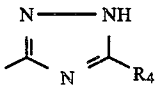
with $R_4$ = H, $NH_2$ (a)

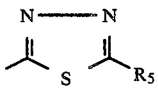
with $R_5$ = $NH_2$, SH (b)

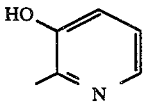
(c)

A represents hydrogen, a cation or an ester or hemiacetal, easily hydrolyzable or metabolically labile and pharmaceutically acceptable.

In the present Application:

the term "cation" denotes an alkaline or alkaline-earth ion, preferably sodium, potassium or calcium ions or the "ammonium" derivative resulting by protonation of a pharmaceutically acceptable amine such as ethylenediamine, ethanolamine, tromethanine and the like or of an amino acid such as lysine, arginine or acetylcysteine, to form addition salts.

The term ester or hemiacetyl, easily hydrolyzable or metabolically labile and pharmaceutically acceptable, denotes radicals such as phthalidyl; pivaloyloxymethyl; acetoxymethyl; ethoxycarbonyloxymethyl; 1-(ethoxycarbonyloxy)-ethyl; acetonyl; $\alpha$-methoxy, $\alpha$-carbomethoxymethyl; carbomethoxymethyl; carbethoxymethyl and the like.

The invention also relates to a process for preparing the compounds of formula (II)

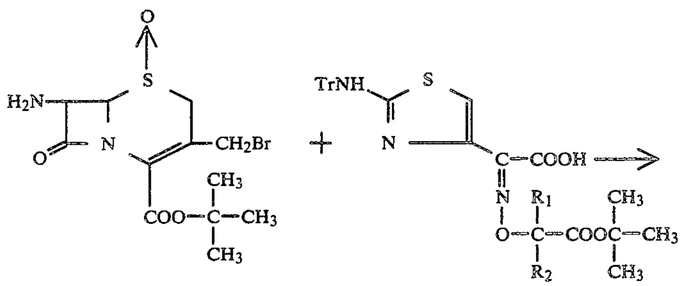

(III) (IV)
Tr = trityl

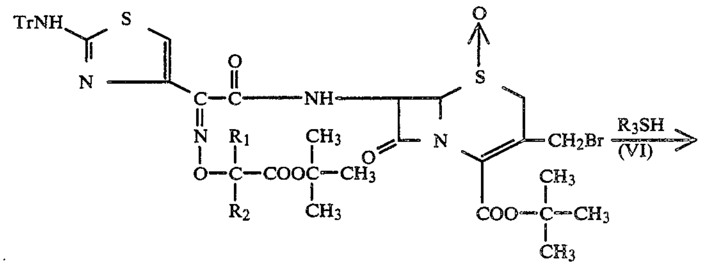

(V)

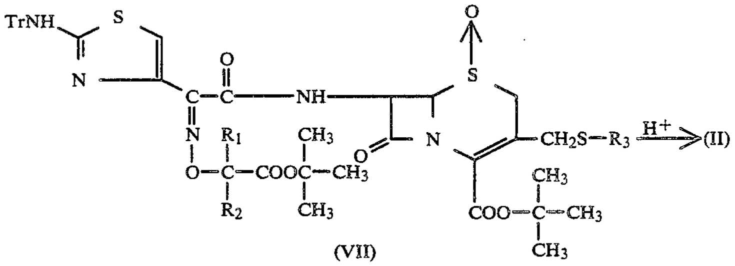

(VII)

The first step consists in acylating the 7-amino 3-bromomethyl 3-cepheme carboxylate of tertiobutyl S-oxide-1 (III) by the acid (IV). Before carrying out the reaction of acylation, it is desirable to substitute the amino group of the acid (IV) by a protector group easy to eliminate subsequently. The groups usually used in organic synthesis for the protection of the amines and in particular the trityl group may be used.

To effect the reaction of acylation, it is necessary to proceed with activation of the carboxyl group of the compound (IV) preferably by conversion of the acid into anhydride by action of a carbodiimide such as dicyclohexylcarbodiimide.

The reaction of activation is carried out within a suitable organic solvent such as tetrahydrofuran at a temperature of between 0° and 50° C. and preferably at ambient temperature. The reaction of activation is possibly facilitated by addition of a hydroxylated derivative such as 1-hydroxide benzotriazole.

The solution of the acylation reagent thus obtained, from which the dicyclohexylurea formed is removed by filtration, is added to a solution of the compound (III) in a solvent such as dimethyl formamide. The addition of the two reagents may also be carried out in reverse order.

By action on the compound (V) thus obtained of a thiol $R_3SH$ (VI) possibly substituted on the heterocycle, the compound (VII) is obtained. The reaction is carried out by contact of the two reagents within a suitable solvent such as dimethylformamide or N,N-dimethylacetamide at a temperature of between 0° and 50° C. and preferably at ambient temperature. Operation is carried out in the presence of an alkaline agent such as triethylamine or bicarbonate of potassium.

The product (VII) is isolated by dilution with water then purified by the usual methods and in particular by chromatography over silica gel.

The thiol may also be replaced by its sodium salt. The same reaction solvents are used and operation is in this case carried out without alkaline agent.

Finally, to arrive at compounds (II), the protector groups on the amine and the carboxyl functions are simultaneously eliminated by a known process, in particular by hydrolysis in acid medium by using a mineral or organic acid such as hydrochloric acid in formic acid or trifluoroacetic acid.

Concerning the raw materials used in this process, compounds (III) and compounds (IV) as well as their derivatives in which the amino group is blocked by a protector group, are known.

Compounds (II) of the invention in which A is other than H, are obtained from compounds (II) in which A is H by reactions known per se. In this way, the mineral salts are obtained by action on compounds (II) in which A=H of a mineral base such as sodium or potassium hydroxide or sodium bicarbonate in equimolecular quantity. The reaction is carried out in a solvent such as water or ethanol and the salt obtained is isolated by evaporation of the solution.

The salts of organic bases or of amino acids are obtained by action, on a solution of the acid (II; A=H) in a solvent or a mixture of suitable solvents, of an equimolecular quantity of the organic base. The salt is isolated by precipitation with ether.

The esters are obtained by the known processes of esterification, for example the action of a halogen derivative on a salt such as the sodium salt of the acid will advantageously be used for example. The reaction will preferably be carried out in a solvent capable of dissolving the starting acid derivative for example in dimethylformamide.

Isomers of syn and anti form are obtained by suitably selecting the reagents.

The following examples will enable the scope of the invention to be more readily understood.

As is usual in this family of compounds, the products according to the invention do not present a clear melting point but only points of decomposition which do not enable them to be characterized.

The products will therefore be characterized by their nuclear magnetic resonance spectrum recorded at 60 MHz, the internal standard being hexamethyldisiloxan.

The following abbreviations will be used:

S: singlet
D: doublet
T: triplet
Q: quadruplet
D of D: doublet of doublet
S.e.: enlarged singlet
M: multiplet
AB: system AB
J: represents the coupling constant Moreover, elementary microanalyses have been made in each case and are in agreement with the formulae indicated.

EXAMPLE 1

7-[2-(2-amino 4-thiazolyl) 2-(2-carboxy 2-propyl oxyimino)acetamido] 3-(1H 1,2,4-triazole 3-yl thiomethyl) 3-cepheme 4-carboxylic S-oxide-1 acid, Syn isomer (CM 40765)

$R_1 = R_2 = CH_3$; A = H; $R_3$ = 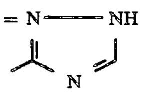 (II)

(a) 7-[2-(2-tritylamino 4-thiazolyl) 2-(2-t-butoxycarbonyl 2-propyl oxyimino)acetamido] 3-bromomethyl 3-cepheme carboxylate of 4-tertiobutyl S-oxide-1, syn isomer $R_1=R_2=CH_3$ (V)

To a solution of 5 g of hydrochloride of 7-amino 3-bromomethyl 3-cepheme carboxylate of 4-tertiobutyl S-oxide-1 in 90 ml of methylene chloride are added 1.72 ml of triethylamine, 7.57 g of 2-(2-tritylamino 4-thiazolyl) 2-(2-t-butoxycarbonyl 2-propyl oxyimino)acetic acid, 2.84 g of dicyclohexylcarbodiimide and 0.1 g of hydroxybenzotriazole. The mixture is stirred for 15 hours at ambient temperature then the dicyclohexylurea formed is filtered.

After evaporation of the solvent, the residue is chromatographed over a column of silica gel (250 g). By eluting with a hexane-ethyl acetate 50-50 (vol/vol) mixture, 4.3 g of the expected product are obtained.

NMR spectrum (in solution in deuterium dimethylsulfoxide) 1H at 8.70 ppm(NH-Trit, S)-1H at 8.07 ppm (NH—CO, D, J=9 Hz)-15H at 7.25 ppm (H trit, S)-1H at 6.72 ppm (H thiazole, S)-1H at 5.88 ppm ($H_7$, D of D, $J_1$=9 Hz, $J_2$=4 Hz)-1H at 4.96 ppm ($H_6$, D, J=4 Hz)-2H at 4.50 ppm ($CH_2Br$, AB, $J_{AB}$=12 Hz)-2H at 3.77 ppm ($CH_2$ in 2, S.e.)-9H at 1.45 ppm

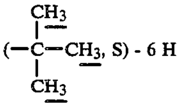

at 1.37 ppm

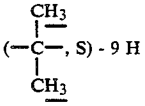

at 1.27 ppm

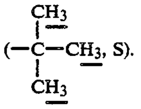

(b) 7-[2-(2-tritylamino 4-thiazolyl) 2-(2-t-butoxycarbonyl 2-propyl oxyimino)acetamido] 3-(1H 1,2,4-triazole 3-yl thiomethyl) 3-cepheme carboxylate of 4-t-butyl S-oxide-1, syn isomer $R_1 = R_2 = CH_3$; $R_3$ = 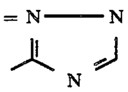 (VII)

To a solution of 2.8 g of the brominated derivative obtained hereinabove in 20 ml of N,N-dimethylacetamide are added 0.308 g of 3-mercapto 1H 1,2,4-triazole then 0.4 ml of triethylamine. After 3 hours of stirring at ambient temperature, the solvent is evaporated in vacuo and the residue is dissolved in 80 ml of methylene chloride. It is chromatographed over a column of 120 g of silica gel. By eluting with ethyl acetate, 2.3 g of the expected product are obtained.

(c) CM 40765

1.06 g of the preceding product is stirred for 30 minutes at ambient temperature in 10 ml of trifluoroacetic acid. The mixture is evaporated in vacuo up to 5–6 ml then precipitated by addition of 200 ml of anhydrous ether. The precipitate is drained, washed with anhydrous ether and dried. The preceding operation is repeated a second time and 0.6 g of the expected product is obtained in the same way.

NMR spectrum 5H between 9 and 10.5 ppm (NH triazole, $NH_2$, 2 COOH, S.e.)-2H at 8.40 ppm (NHCO, H triazole, M)-1H at 6.87 ppm (H thiazole, S)-1H at 5.97 ppm ($H_7$, M)-1H at 4.92 ppm ($H_6$, D, J=4 Hz)-1H at 4.5 ppm ($CH_2S$—, A of AB, $J_{AB}$=13 Hz)-1H at 4.30 ppm ($CH_2S$, B of AB, $J_{AB}$=13 Hz)-2H at 3.80 ppm ($CH_2S$→O, S.e.)-6H at 1.45 ppm

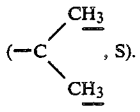

EXAMPLE 2

7-[2-(2-amino 4-thiazolyl) 2-(2-carboxy 2-propyl oxyimino)acetamido] 3-(2-amino 1,3,4-thiazol 5-yl thiomethyl) 3-cepheme 4-carboxylic S-oxide-1 acid, syn isomer (CM 40803)

$R_1 = R_2 = CH_3$; A = H; $R_3$ = 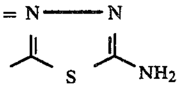 (II)

(a) 7-[2-(2-tritylamino 4-thiazolyl) (2-t-butoxycarbonyl oxyimino)acetamido] 3-(2-amino 1,3,4-thiadiazol 5-yl thiomethyl) 3-cepheme carboxylate of 4-t-butyl S-oxide-1, syn isomer $R_1 = R_2 = CH_3$; $R_3$ = 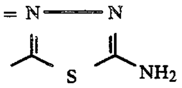 (VII)

The mixture of 1 g of the brominated derivative of Example 1(a)-, 0.18 g of 2-amino 5-mercapto 1,3,4-thiadiazole and 0.12 g of potassium dicarbonate in 10 ml of dimethylformamide is stirred for 16 hours at ambient temperature. The solvent is evaporated in vacuo and the residue is dissolved in methylene chloride. The solution is washed with water then with a saturated sodium chloride aqueous solution. It is dried over magnesium sulfate then the solution is concentrated to 5 ml. It is chromatographed over a column of 25 g of silica gel. By eluting with an ethyl acetate-hexane 90-10 (vol/vol) mixture, 1 g of the expected product is obtained.

(b) CM 40 803

The mixture of 0.55 g of the protected product obtained hereinabove and 6 ml of trifluoroacetic acid is stirred for 45 minutes at 20° C. It is concentrated in vacuo to about 3 ml then precipitated by addition of ether. The solid is drained and dried over phosphoric anhydride. 0.39 g of the expected product are obtained.

NMR spectrum 1H at 8.5 ppm (NHCO, D, J=9 Hz)-6H between 6.5 and 8.5 ppm (2 $NH_2$, 2 COOH, M)-1H at 6.90 ppm (H thiazole, S)-1H at 5.97 ppm ($H_7$, M)-1H at 4.96 ppm ($H_6$, D, J=4 Hz)-1H at 4.45 ppm ($CH_2S$, A of AB, $J_{AB}$=13 Hz)-1H at 3.90 ppm ($CH_2S$,B of AB, $J_{AB}$=13 Hz)-2H at 3.85 ppm ($CH_2S$→O, S.e.)-6H at 1.45 ppm

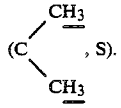

EXAMPLES 3 TO 5

Operation is carried out as in Example 2(a)—from the brominated derivative of Example 1(a)—but varying the nature of the thiol used.

By then carrying out deprotection of the products obtained as indicated in Example 2(b), the different compounds (II) mentioned in Table 1 are obtained.

TABLE 1

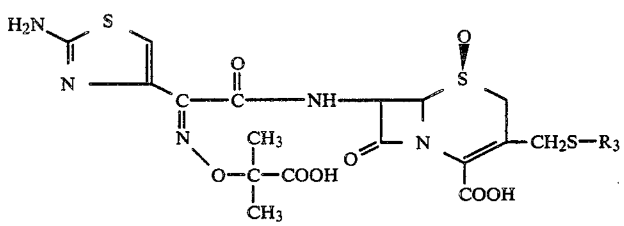

| Example No. | Code No. of product | $R_3$ | NMR spectrum |
|---|---|---|---|
| 3 | 40.804 | 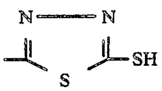 | 1 H at 8.40 ppm (NHCO, D, J = 9 Hz - 4 H between 8.5 and 10 ppm ($NH_2$, 2 COOH) - 1 H at 6.83 ppm (H thiazole, S) - 1 H at 5.96 ppm ($H_7$, D of D, $J_1$ = 9 Hz, $J_2$ = 4 Hz) - 1 H at 4.93 ppm ($H_6$, D, J = 4 Hz) - 1 H at 4.60 ppm ($CH_2S$, A of AB, $J_{AB}$ = 13 Hz) - 1 H at 4.05 ppm ($CH_2S$, B of AB, $J_{AB}$ = 13 Hz) - 2 H at 3.81 ppm ($CH_2S$→O, S.e.) - 6 H at 1.42 ppm |

TABLE 1-continued

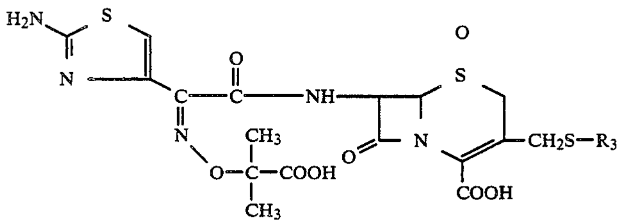

| Example No. | Code No. of product | $R_3$ | NMR spectrum |
|---|---|---|---|
| | | | (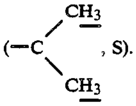, S). |
| 4 | 40 805 | 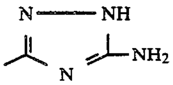 | 7 H between 8 and 10 ppm (NH triazole, 2 $NH_2$, 2 COOH, S.e.) - 1 H at 8.45 ppm (NHCO, D, J = 9 Hz) - 1 H at 6.85 ppm (H thiazole, S) - 1 H at 5.97 ppm ($H_7$, D of D, $J_1$ = 9 Hz, $J_2$ = 4 Hz) - 1 H at 4.95 ppm ($H_6$, D, J = 4 Hz) - 1 H at 4.30 ppm ($CH_2S$, A of AB, $J_{AB}$ = 13 Hz) - 1 H at 3.90 ppm ($CH_2S$, B of AB, $J_{AB}$ = 13 Hz) - 2 H at 3.85 ppm ($CH_2S \rightarrow O$, S.e.) - 6 H at 1.45 ppm (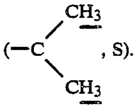, S). |
| 5 | 40 953 | 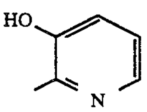 | 5 H at 9.0 ppm (2 COOH, $NH_2$, OH, M) - 1 H at 8.43 ppm (NHCO, D, J = 9 Hz) - 1 H at 7.87 ppm ($H_6$ pyridine, M) - 3 H at 6.95 ppm ($H_4$ and $H_5$ pyridine, H thiazole, M) - 1 H at 5.95 ppm ($H_7$, D of D, $J_1$ = 9 Hz, $J_2$ = 5 Hz) - 1 H at 4.95 ppm ($H_6$, D, J = 5 Hz) - 1 H at 4.60 ppm ($CH_2S$, A of AB, $J_{AB}$ = 13 Hz) - 3 H at 3.80 ppm ($CH_2S \rightarrow O$ and $CH_2S$, B of AB, M) - 6 H at 1.45 ppm (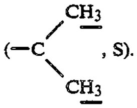, S). |

EXAMPLE 6

7-[2-(2-amino 4-thiazolyl) 2-(1-carboxy cyclobutyl oxyimino)acetamido] 3-(3-hydroxy 2-pyridinyl thiomethyl) 3-cepheme 4-carboxylic S-oxide-1 acid, syn isomer (CM 41646)

$R_1 + R_2 = (CH_2)_3$; $R_3$ = 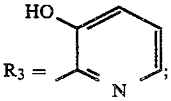; A = H

(a) 7-[2-(2-tritylamino 4-thiazolyl) 2-(1-t-butoxycarbonyl 1-cyclobutyl oxyimino)acetamido] 3-bromomethyl 3-cepheme carboxylate of 4-t-butyl S-oxide-1, syn isomer $R_1+R_2=(CH_2)_3$ (V)

To a solution of 4.4 g of hydrochloride of 7-amino 3-bromomethyl 3-cepheme carboxylate of t-butyl S-oxide-1 in 70 ml of anhydrous methylene chloride, are added, in a nitrogen atmosphere, 1.5 ml of triethylamine, 5.1 g of 2-(2-tritylamino 4-thiazolyl) 2-(1-t-butoxycarbonyl 1-cyclobutyl oxyimino)acetic acid, syn isomer, 2.4 g of dicyclohexylcarbodiimide and 0.1 g of 1-hydroxy benzotriazole. The mixture is stirred for 1 hour at ambient temperature then the dicyclohexylurea formed is filtered and the solution is concentrated to 20 ml in vacuo.

It is chromatographed over a column of silica gel (150 g). By elution with the hexane-ethyl acetate 40–60 (vol/vol) mixture, 4.8 g of the expected product are obtained after evaporation of the solvent.

NMR spectrum 1H at 7.90 ppm (N$\underline{H}$CO, D, J=9 Hz)-15H at 7.26 ppm (aromatic H, S)-1H at 6.97 ppm (N$\underline{H}$-trityl, S.e.)-1H at 6.65 ppm (H thiazole, S)-1H at 6.18 ppm ($H_7$, D of D, $J_1$=9 Hz, $J_2$=4.5 Hz)-2H at 3.4 ppm ($CH_2S$→O, S.e.)-6 H between 1.5 and 2.6 ppm (cyclobutyl, M)-9H at 1.46 ppm

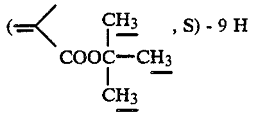

at 1.36 ppm

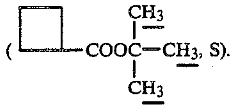

(b) 7-[2-(2-tritylamino 4-thiazolyl) 2-(1-t-butoxycarbonyl 1-cyclobutyl oxyimino)acetamido] 3-(3-hydroxy 2-pyridinyl thiomethyl) 3-cepheme carboxylate of 4-t-butyl S-oxide-1, syn isomer To a solution of 0.164 g of 3-hydroxy 2-mercapto pyridine in 6 ml of dimethylformamide are added 0.128 g of potssium bicarbonate then 1 g of the brominated derivative obtained hereinabove. The mixture is stirred for 16 hours at ambient temperature then poured into 50 ml of ice water. The precipitate is drained and washed with water. The solid is redissolved in methylene chloride, the solution is dried over magnesium sulfate and concentrated to 5 ml. It is chromatographed over a column of 20 g of silica gel. By eluting with the hexane-ethyl acetate 40–60 (vol/vol) mixture, 0.85 g of the expected product is obtained.

(c) CM 41646

The solution of 0.8 g of the product obtained in (b) in 8 ml of trifluoroacetic acid is left at ambient temperature for 45 minutes. It is evaporated to dryness in vacuo and the residue is triturated with ether. The solid is drained and dried in vacuo in the presence of phosphoric anhydride to obtain 0.5 g of the expected product.

NMR spectrum 1H at 10.40 ppm (O$\underline{H}$, S.e.)-1H at 8.70 ppm (N$\underline{H}$CO, D, J=8 Hz) 1H at 7.80 ppm ($H_6$' pyridine, D, J=5 Hz)-2H at 7.10 ppm ($NH_2$, S.e.)-2H at 6.95 ppm ($H_4$' and $H_5$' pyridine, M)-1H at 6.80 ppm (H, thiazole, S)-1H at 5.90 ppm ($H_7$, D of D, $J_1$=8 Hz, $J_2$=5 Hz)-1H at 4.95 ppm ($H_6$, D, J=5 Hz)-1H at 4.65 ppm ($C\underline{H}_{(2)}S$, D, J=14 Hz)-3H at 3.80 ppm ($CH_2S$→O and $C\underline{H}_{(2)}S$, M)-4H at 2.40 ppm

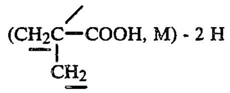

at 1.90 ppm

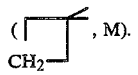

Products (II) have been studied as far as their pharmacological properties and more especially their bacteriostatic action are concerned.

Bacteriostatic action in vitro was determined in a solid medium by the dilutions method. The results obtained are expressed in minimum inhibitory concentrations (MIC-μg/ml) and concern different strains of Enterobacteria and of Pseudomonas.

By way of comparison, the results obtained with two similar products described in the prior art (Belgian Pat. No. 866 038) have been added, namely:

7-[2-(2-amino 4-thiazolyl) 2-carboxymethoxyimino acetamido] 3-(2-pyridyl thiomethyl) 3-cepheme 4-carboxylic S-oxide-1 acid, syn isomer:

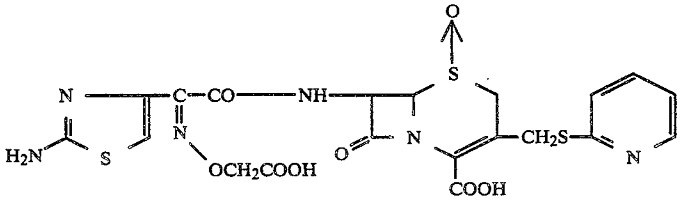

(compound A)

7-[2-(2-amino 4-thiazolyl) 2-methoxyimino acetamido] 3-(1,2,4-triazol 3-yl thiomethyl) 3-cephem 4-carboxylic S-oxide-1 acid, syn isomer

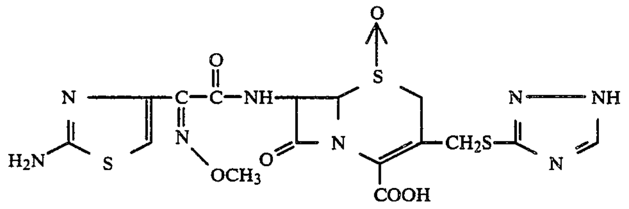

(compound B)

The results obtained are shown in Table 2. These results show that the products according to the invention have an interesting activity on strains which are usually hardly sensitive to the antibiotics of the cephalosporin family, namely Enterobacteria and Pseudomonas.

With respect to the reference products A and B, products (II) show a surprizing activity on the strains of Pseudomonas, good activity on Enterobacter while having an activity at least equal to that of the reference products with respect to Proteus, Serratia and *Escherichia coli.*

Furthermore, tests made on animals have shown no toxicity in the products according to the invention.

The products of the invention may therefore be used as antibiotics in human or veterinary medicine. They may be used in all sensitive-germ bacterial infections.

The pharmaceutical compositions are made from compounds (II) in their acid form or, when their solubility is insufficient, in the form of a salt.

The pharmaceutical compositions may be solid or liquid and are for example in the form of tablets, capsules, granules, ointments, creams, gels or injectable preparations.

Dosage may vary to considerable proportions, depending on the type and seriousness of the infection to be treated and depending on the mode of administration. It is most often between 0.250 g and 4 g per day in the adult, by the injectable route.

By way of example of pharmaceutical composition containing one of the products of the invention, injectable ampoules containing:

CM 40953: 1 g
Water for injectable preparation 5 ml
Sodium carbonate qs pH=6.5
may be prepared.

TABLE 2

| | Product | | | | | | | |
|---|---|---|---|---|---|---|---|---|
| Strain | 40765 | 40803 | 40804 | 40805 | 40953 | 41646 | A | B |
| Pseudomonas RL 112 | 4 | 4 | 8 | 4 | 8 | 16 | 256 | 512 |
| Pseudomonas 8203 | 8 | 4 | 8 | 4 | 16 | 16 | 256 | 256 |
| Pseudomonas 526 | 8 | 4 | 8 | 4 | 16 | 16 | >256 | 512 |
| Pseudomonas A 22 IP | 8 | 8 | 8 | 8 | 16 | 32 | >256 | 512 |
| Pseudomonas 103 IFE | 8 | 4 | 8 | 8 | 16 | 16 | >256 | 256 |
| Proteus 1510 | 0.125 | ≦0.125 | ≦0.125 | ≦0.125 | ≦0.125 | — | 0.25 | 0.25 |
| Serratia RL 72 | 4 | 1 | 4 | 4 | 8 | 8 | 32 | 8 |
| Enterobacter P 99 | 8 | 2 | 4 | 2 | 8 | — | 16 | 32 |

What is claimed is:

1. A cephalosporin having the formula:

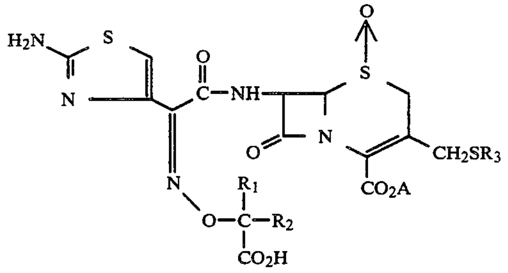

wherein $R_1$ and $R_2$, taken separately, each represent a methyl group or $R_1$ and $R_2$ taken together represent at 1,3-propylene group, $R_3$ is a hydroxypyridyl group of formula

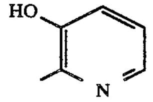, and

A is selected from the group consisting of hydrogen;

alkali metal ions;

substituted ammonium ions resulting from protonation of an amine selected from the group consisting of ethylene diamine, ethanolamine, tromethamine, lysine, arginine, and acetylcysteine;

tertiary butyl; and organic radicals selected from the group consisting of phthalidy, pivaloyloxymethyl, acetoxymethyl, ethoxycarbonyloxymethyl, 1-(ethoxycarbonyloxy)-ethyl, acetonyl, α-methoxy-α-carbomethoxymethyl, carbomethoxymethyl, and carbethoxymethyl;

or a phramaceutically acceptable acid addition salt of the compound in which A is H, tertiary butyl, or said organic radicals.

2. A cephalosporin according to claim 1, in which the oximino substituent is in the syn isomeric form.

3. A pharmaceutical composition having antibacterial action, comprising at least one cephalosporin according to claim 1, plus a pharmaceutically acceptable carrier.

4. A pharmaceutical composition of claim 3, in which the active ingredient is the product in which $R_1$ and $R_2$ are $CH_3$, and A is H.

5. A pharmaceutical composition having antibacterial action comprising at least one cephalosporin according to claim 2, plus a pharmaceutically acceptable carrier.

6. A pharmaceutical composition according to claim 5 in which the active ingredient is the product in which $R_1$ and $R_2$ are $CH_3$, and A is H.

* * * * *